(12) United States Patent
Thomson

(10) Patent No.: US 6,211,407 B1
(45) Date of Patent: Apr. 3, 2001

(54) DICREATINE CITRATE AND TRICREATINE CITRATE AND METHOD OF MAKING SAME

(75) Inventor: James Kenneth Thomson, Wadsworth, IL (US)

(73) Assignee: Pfanstiehl Laboratories, Inc., Waukegan, IL (US)

( * ) Notice: Subject to any disclaimer, the term of this patent is extended or adjusted under 35 U.S.C. 154(b) by 0 days.

(21) Appl. No.: 09/563,980

(22) Filed: May 3, 2000

(51) Int. Cl.⁷ .................................................. C07C 241/00
(52) U.S. Cl. ............................................ 562/560; 562/584
(58) Field of Search ..................................... 562/560, 584

(56) References Cited

U.S. PATENT DOCUMENTS

| | | | |
|---|---|---|---|
| 5,863,939 | * | 1/1999 | Pischel et al. . |
| 5,886,040 | * | 3/1999 | Fang . |
| 5,925,378 | | 7/1999 | Carnazzo . |
| 5,973,199 | | 10/1999 | Negrisoli et al. . |
| 5,994,581 | * | 11/1999 | Fang . |

\* cited by examiner

*Primary Examiner*—Paul J. Killos
*Assistant Examiner*—Mahreen Chaudhry
(74) *Attorney, Agent, or Firm*—Wallenstein & Wagner, Ltd.

(57) ABSTRACT

A dicreatine citrate or tricreatine citrate, comprising two and three creatine cations per citrate anion, respectively. The dicreatine citrate has a melting point of about 146° F., and the tricreatine citrate has a melting point of about 154° F.

4 Claims, No Drawings

DICREATINE CITRATE AND TRICREATINE CITRATE AND METHOD OF MAKING SAME

TECHNICAL FIELD

This invention relates to novel compounds, dicreatine and tricreatine citrate, and a method of making those products.

BACKGROUND OF THE INVENTION

Creatine monohydrate (hereinafter "creatine") is a naturally occurring metabolite found in red muscle tissue. It plays an important role in energizing the muscle. Creatine phosphate is used by the body to recycle ADP to ATP (adenosine triphosphate). ATP is stored in the mitochondria of muscle cells and produces energy when converted into ADP. Muscle fatigue begins when the supply of ATP is lowered.

Synthetic or man-made creatine monohydrate is widely available. Persons interested in and engaging in regular weight lifting regimens for the purpose of body building find that shortly after beginning the use of creatine as a nutritional supplement, muscles take on additional mass and definition.

Synthetic creatine monohydrate is sold in powder form. The powder may be blended with juices or other fluids, and then promptly ingested. Prompt ingestion is important, because creatine is not stable in acidic solutions, such as juices. If creatine is retained in acidic solutions for even relatively short periods of time, most or all of the creatine in this solution turns into creatinine. Creatinine does not have the beneficial effects of creatine.

Creatine monohydrate can be used to manufacture various salts. These salts include, for example, citric and maleic salts.

U.S. Pat. No. 5,973,199 (hereinafter "the '199 patent") discloses a form of a creatine salt that appears to be a combination of one mole of creatine monohydrate with one mole of citric acid, i.e., a monocreatine citrate. Particularly, Example 1 of the '199 patent discloses the combination of 0.180 moles of monohydrate citric acid with 0.134 moles of creatine monohydrate. A two-to-one or three-to-one molar ratio of creatine to the citric acid would be necessary for the production of a dicreatine or tricreatine salt. Such salts do not appear to be disclosed in the '199 patent.

U.S. Pat. No. 5,925,378 (hereinafter the '378 patent) discloses another form of a creatine citrate. In the '378 patent, as in the '199 patent, there is no disclosure of a creatine citrate that includes a two to one or three to one or more molar ratio of creatine monohydrate to the citric acid, i.e., there is no disclosure of a dicreatine or tricreatine citrate.

It would be desirable to provide another form of creatine that is stable, and that can prevent or impede the conversion of creatine to creatinine. It would further be desirable to provide a form of creatine salt that is other than a monocreatine citrate form of the salt.

SUMMARY OF THE INVENTION

The invention is a dicreatine citrate comprising two creatine cations per citrate dianion. The dicreatine citrate has a melting point of approximately 146° F. The invention is also a tricreatine citrate comprising three creatine cations per citrate trianion. The tricreatine citrate has a melting point of approximately 154° F.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

EXAMPLE 1

Large scale quantities of the dicreatine citrate of the invention may be made as follows.

A reactor is charged with 2,400 gallons of anhydrous methanol.

With stirring, 1,315 kilograms (6,845 moles) of citric acid is added to the methanol. Citric acid has a molecular weight of 192.11, and is available commercially. Stirring should be continued for thirty (30) minutes after all of the citric acid has been added to the methanol.

After the thirty (30) minutes have passed, with continued agitation, creatine monohydrate is added to the methanol/citric acid mixture. The creatine monohydrate is available as Catalog No. C-114 from Pfanstiehl Laboratories, Waukegan, Ill. In this embodiment, 2,041 kg of the creatine monohydrate is added. After all of the creatine monohydrate has been added, the stirring continues for approximately four (4) hours.

Creatine monohydrate has a molecular weight of 149.13, therefore the amount of creatine monohydrate added is 13,686 gram-moles. Accordingly, given that this reaction mixture includes 6,845 moles of citric acid, the stoichiometric ratio of creatine to citric acid is 2:1.

The finished product is accordingly a dicreatine citrate, having two creatine cations per citrate dianion.

The crystallized product dicreatine citrate is filtered from the reaction mixture using a centrifuge. Each centrifuge load is washed with anhydrous methanol to remove any byproducts.

The solid dicreatine citrate product is dried at 45°±5° C. to an LOD of less than 3%.

The product is ground to a free flowing consistency and packaged.

The melting point of the dicreatine citrate in accordance with the invention is approximately 146° C. This is significantly higher than the melting points of the monocreatine citrates of the '199 patent, implying significant differences in physical properties of the compositions claimed in the '199 patent versus the compositions of the present invention. An assay for the creatine content in the product gives a value of approximately 57.7%. The monocreatine citrate would give a value of approximately 40.6%.

EXAMPLE 2

Tricreatine citrate may be manufactured using the same procedure but changing the ratio of creatine to citric acid.

Five liters of anhydrous methanol are charged to a clean reactor.

With stirring, 500 grams of anhydrous citric acid (2.6 moles) are added to the anhydrous methanol. The resulting mixture is stirred for thirty (30) minutes.

One thousand one hundred and sixty-three (1,163) grams (7.8 moles) of creatine monohydrate are added to the citric acid/methanol mixture. This mixture is stirred for approximately four (4) hours.

After the four hours have passed, the product is filtered and washed with methanol.

The finished product is dried. The melting point of the tricreatine citrate is 154° C. The creatine assay for the material is approximately 67.2%.

While the specific embodiments have been illustrated and described, numerous modifications come to mind without significantly departing from the spirit of the invention and the scope of protection is only limited by the scope of the accompanying claims.

What I claim is:

1. A dicreatine citrate, said dicreatine citrate comprising two creatine cations per citrate dianion.

2. The dicreatine citrate of claim 1, wherein said dicreatine citrate has a melting point of approximately 146° C. and a creatine content of 57.7% (wt.).

3. A tricreatine citrate said tricreatine citrate comprising three creatine cations per citrate trianion.

4. The tricreatine citrate of claim 3, wherein said tricreatine citrate has a melting point of approximately 154° C. and a creatine content of 67.2% (wt.).

* * * * *

UNITED STATES PATENT AND TRADEMARK OFFICE
CERTIFICATE OF CORRECTION

PATENT NO. : 6,211,407 B1  
DATED : April 3, 2001  
INVENTOR(S) : James Kenneth Thomson Page 1 of 1

It is certified that error appears in the above-identified patent and that said Letters Patent is hereby corrected as shown below:

<u>Column 4, claim 2,</u>  
Lines 4 to 5, change "discreatine" to -- dicreatine --.

Signed and Sealed this

Eighth Day of January, 2002

*Attest:*

JAMES E. ROGAN  
*Director of the United States Patent and Trademark Office*

*Attesting Officer*